United States Patent
Nasu

(10) Patent No.: US 11,208,378 B2
(45) Date of Patent: Dec. 28, 2021

(54) ALKOXYMETHYL-SUBSTITUTED BISPHENOL COMPOUND

(71) Applicant: HONSHU CHEMICAL INDUSTRY CO., LTD., Tokyo (JP)

(72) Inventor: Akihito Nasu, Wakayama (JP)

(73) Assignee: HONSHU CHEMICAL INDUSTRY CO., LTD., Tokyo (JP)

(*) Notice: Subject to any disclaimer, the term of this patent is extended or adjusted under 35 U.S.C. 154(b) by 22 days.

(21) Appl. No.: 16/475,637

(22) PCT Filed: Jan. 11, 2018

(86) PCT No.: PCT/JP2018/000486
§ 371 (c)(1),
(2) Date: Jul. 2, 2019

(87) PCT Pub. No.: WO2018/135373
PCT Pub. Date: Jul. 26, 2018

(65) Prior Publication Data
US 2021/0053916 A1    Feb. 25, 2021

(30) Foreign Application Priority Data

Jan. 17, 2017 (JP) .............................. JP2017-005490

(51) Int. Cl.
*C07C 317/22* (2006.01)

(52) U.S. Cl.
CPC .................. *C07C 317/22* (2013.01)

(58) Field of Classification Search
CPC .................................................. C07C 317/22
See application file for complete search history.

(56) References Cited

U.S. PATENT DOCUMENTS

| | | | |
|---|---|---|---|
| 3,230,198 A | 1/1966 | Meyers | |
| 4,975,470 A * | 12/1990 | Matzner | C08L 69/00 521/134 |
| 2005/0272957 A1 * | 12/2005 | Gao | C07C 315/04 568/53 |
| 2012/0181251 A1 | 7/2012 | Minegishi et al. | |
| 2019/0136056 A1 * | 5/2019 | Jeol | C08L 81/02 |

FOREIGN PATENT DOCUMENTS

| | | |
|---|---|---|
| JP | 2009265445 A | 11/2009 |
| JP | 2015114355 A | 6/2015 |
| WO | 2011040340 A1 | 4/2011 |

OTHER PUBLICATIONS

International Search Report (ISR) dated Apr. 17, 2018, issued for International application No. PCT/JP2018/000486. (1 page).

Notification Concerning Transmittal of International Preliminary Report on Patentability (PCT/IB/326) and Notification of Transmittal of Translation of the International Preliminary Report on Patentability (PCT/IB/338) dated Aug. 1, 2019, with International Preliminary Report on Patentability (PCT/IB/373) and Written Opinion of the International Searching Authority (PCT/ISA/237), for corresponding international application PCT/JP2018/000486, (11 pages).

* cited by examiner

*Primary Examiner* — Rosalynd A Keys
(74) *Attorney, Agent, or Firm* — Law Office of Katsuhiro Arai

(57) ABSTRACT

The present invention addresses the problem of providing a novel alkoxymethyl-substituted bisphenol compound having exceptional storage stability and exceptional solvent solubility, heat resistance, and optical properties when used as a resin raw material. This problem can be solved by using an alkoxymethyl-substituted bisphenol compound represented by General Formula (1):

General Formula (1)

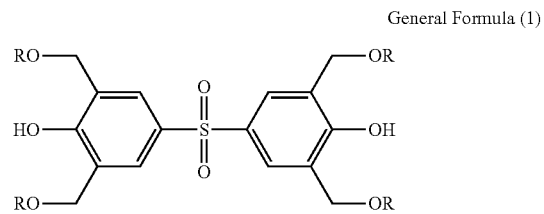

(wherein each R independently represents an alkyl group having 1 to 4 carbon atoms).

1 Claim, No Drawings

ALKOXYMETHYL-SUBSTITUTED BISPHENOL COMPOUND

CROSS REFERENCE TO RELATED APPLICATIONS

This application is the U.S. National Phase under 35 U.S.C. § 371 of International Application PCT/JP2018/000486, filed Jan. 11, 2018, which claims priority to Japanese Patent Application No. 2017-005490, filed Jan. 17, 2017. The International Application was published under PCT Article 21(2) in a language other than English.

TECHNICAL FIELD

The present invention relates to a novel alkoxymethyl-substituted bisphenol compound. Specifically, the present invention relates to an alkoxymethyl-substituted bis(4-hydroxyphenyl)sulfone compound.

BACKGROUND ART

Conventionally, bisphenol compounds are widely used as raw materials for thermoplastic engineering resins such as polycarbonate and polyacrylate, thermosetting resins such as epoxy resin and polyimide resin, and further photosensitive resists, epoxy resin, curing agents for these, color developers for thermal recording, anti-fading agents, storage stabilizers, anti-oxidants, bactericides, fungicides, and so forth.

In recent years, particularly in the field of electric and electronic devices, accompanied by miniaturization of and improvement in the performance of devices and electronic elements, improvement in heat resistance, solvent resistance, optical characteristics, and so forth has been increasingly demanded, and in particular, in a manufacturing process of semiconductor devices, microfabrication by lithography using a photoresist composition is performed, and development of resins and additives compatible with various lithography techniques is made.

With the progress of processing technology, problems such as resist pattern collapse due to increase in aspect ratio, and notching caused by reflection of exposure light from a substrate has become non-negligible. As a method to solve these problems, antireflective films and processes using a resist underlayer film such as a multilayer resist process have been developed, and for the resist underlayer film, characteristic functions such as high heat resistance having an etching rate different from an upper layer resist, optical properties, and so forth are required.

Along with that, also from the viewpoint of the bisphenol compound used as a raw material, a new bisphenol compound is also required for resins and additives to be used to meet the demand for higher performance and higher functionality.

Among such bisphenol compounds, bis[3,5-bis(methoxymethyl)-4-hydroxyphenyl]ether, bis[3,5-bis(methoxymethyl)-4-hydroxyphenyl]sulfide (Patent Literature 1), and so forth are known as compounds which are tetra-alkoxymethyl-substituted bisphenol compounds and contain a hetero atom in the central skeleton thereof.

However, further improvement is required for the conventionally known compounds that have poor heat resistance and storage stability, are difficult to crystallize, and can not be easily purified, and compounds with higher performance are demanded particularly for application as photosensitive materials.

CITATION LIST

Patent Literature

Patent Literature 1: WO 2011/040340

SUMMARY OF THE INVENTION

Technical Problems

An object of the present invention is to provide a novel alkoxymethyl-substituted bisphenol compound which is excellent in storage stability and excellent in heat resistance and optical properties when used as a raw material for resin.

Solution to Problems

As a result of intensive studies to solve the above problems, the present inventors found that an alkoxymethyl-substituted bisphenol compound excellent in heat resistance, storage stability, and so forth can be obtained by introducing an alkoxymethyl group to a position adjacent to two hydroxy groups in a bisphenol compound having a sulfonyl group in the central skeleton thereof, and thus completed the present invention.

The present invention is as follows.

1. An alkoxymethyl-substituted bisphenol compound represented by General Formula (1)

[Chem. 1]

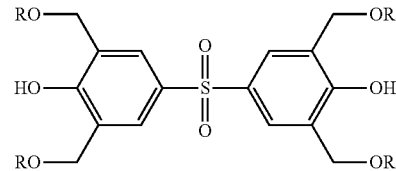

General Formula (1)

(wherein each R independently represents an alkyl group having 1 to 4 carbon atoms).

Advantageous Effects of Invention

The alkoxymethyl-substituted bisphenol compound of the present invention, that is, 1,1-bis[3,5-di(alkoxymethyl)-4-hydroxyphenyl]sulfone can be obtained as a crystallized compound by crystallization, therefore is easy to purify, and itself is excellent in the storage stability, heat resistance, and thermal stability.

In addition, when the alkoxymethyl-substituted bisphenol compound of the present invention is used as a raw material for resin, the resulting resin has a sulfonyl group in the central skeleton thereof, and is therefore expected to be excellent in heat resistance, optical properties, and so forth. Therefore, when the alkoxymethyl-substituted bisphenol compound of the present invention is used, for example, as an additive (crosslinking agent) for a resin for a resist underlayer film, improvement in etching rate and high heat resistance can be expected, and thus the alkoxymethyl-substituted bisphenol compound of the present invention can be advantageously used as an additive or a crosslinking agent for phenol resin, epoxy resin, and the like.

DESCRIPTION OF EMBODIMENTS

The alkoxymethyl-substituted bisphenol compound of the present invention is represented by General Formula (1)

shown above, and each R in the formula independently represents an alkyl group having 1 to 4 carbon atoms. Specifically, the alkyl group having 1 to 4 carbon atoms is a methyl group, an ethyl group, a propyl group or a butyl group, and the alkyl group having 3 or more carbon atoms may be linear or branched. R is preferably a primary or secondary alkyl group, and particularly preferably a methyl group. The alkyl group may have a substituent such as, for example, a phenyl group or an alkoxy group, as long as the effects of the present invention are not impaired. The four Rs in General Formula (1) shown above are preferably the same alkyl group.

Therefore, preferred specific examples of the alkoxymethyl-substituted bisphenol compound of the present invention include bis[3,5-bis(methoxymethyl)-4-hydroxyphenyl]sulfone,

[Chem. 2]

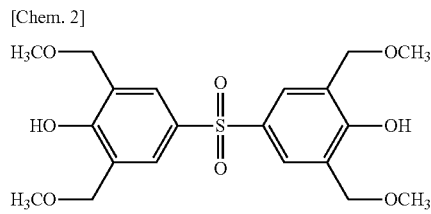

bis[3,5-bis(ethoxymethyl)-4-hydroxyphenyl]sulfone, and bis[3,5-bis (isopropyloxymethyl)-4-hydroxyphenyl]sulfone.

The method for producing the alkoxymethyl-substituted bisphenol compound represented by General Formula (1) shown above of the present invention is not particularly limited, and production can be performed by using a known method.

However, from the viewpoint that the reaction yield is high, high-purity products can be obtained, and industrial production is easy, and so forth, as a method for producing an alkoxymethyl-substituted bisphenol compound, a method of producing the alkoxymetyl-substituted bisphenol compound of the present invention represented by General Formula (1) by, in a solvent, reacting (aminomethylating) 1,1-bis(4-hydroxyphenyl)sulfone, which is a corresponding bisphenol represented by Chemical Formula (2) shown below,

[Chem. 3]

Chemical Formula (2)

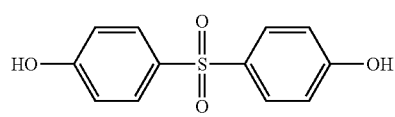

with formaldehyde and a secondary amine to obtain an aminomethyl-substituted bisphenol compound (Step 1), then acyloxylating an aminomethyl group (Step 2), and alkoxyethylating an acyloxy group (Step 3) is preferable. Hereinafter, this production method will be described in detail. The alkoxymethyl-substituted bisphenol compound of the present invention obtained by this production method is normally obtained as a crystallized product with a purity of 90% or higher, and is therefore industrially easy to handle and excellent in storage stability.

In the preferable method for producing the alkoxymethyl-substituted bisphenol compound of the present invention, a reaction formula for the case where the secondary amine is diethylamine, the carboxylic acid anhydride is acetic anhydride, and the alkyl alcohol is methanol is shown below.

[Chem. 4]

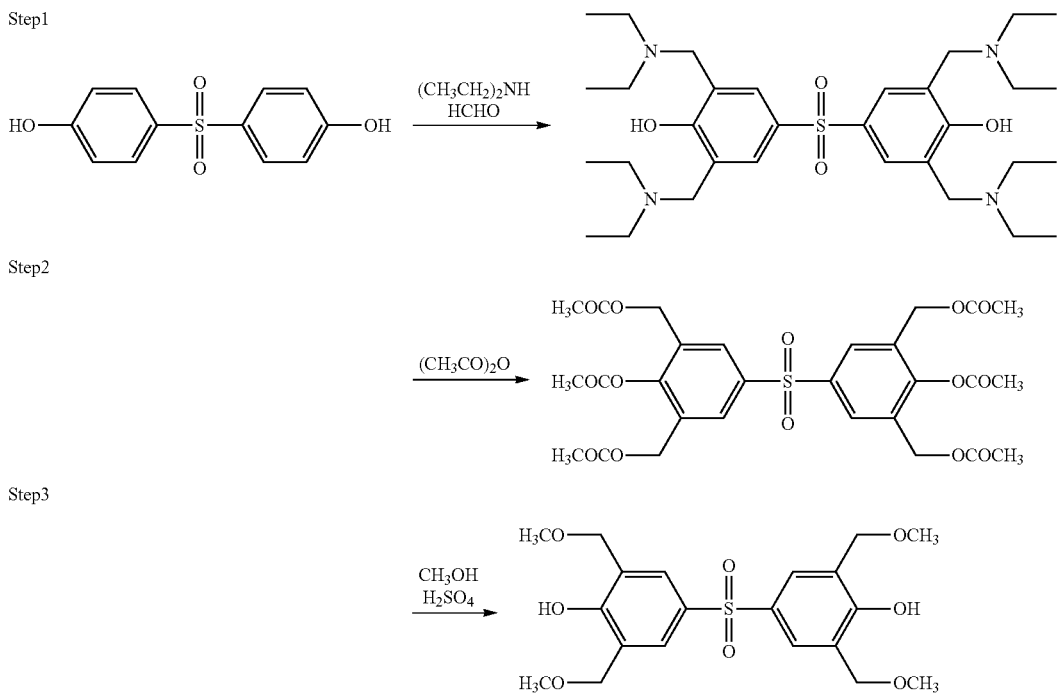

The above-mentioned preferable method for producing the alkoxymethyl-substituted bisphenol compound of the present invention will be described in further detail.
<Step 1>
In the step 1 of reacting the bisphenol represented by Chemical Formula (2) as a raw material with formaldehyde and a secondary amine represented by General Formula (3) below in a solvent to obtain an aminomethyl-substituted bisphenol compound represented by General Formula (4) below, the reaction can be easily carried out by a method according to a known Mannich reaction.

The secondary amine used in the above reaction is represented by General Formula (3) below

[Chem. 5]

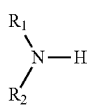

General Formula (3)

(wherein, $R_1$ and $R_2$ each independently represent an alkyl group, a cycloalkyl group, an aralkyl group, or an aryl group, and may contain a hetero atom, and $R_1$ and $R_2$ may bond to each other to form a ring).

As the secondary amine represented by the above General Formula (3), any secondary amine known can be used in the reaction, and specific examples thereof include dimethylamine, diethylamine, dibutylamine, diisopropylamine, pyrrolidine, piperidine, piperazine, and morpholine. In addition, the formaldehyde may be an aqueous solution of formaldehyde or paraformaldehyde.

Accordingly, the aminomethyl-substituted bisphenol compound obtained in the step 1 mentioned above is represented by General Formula (4) below.

[Chem. 6]

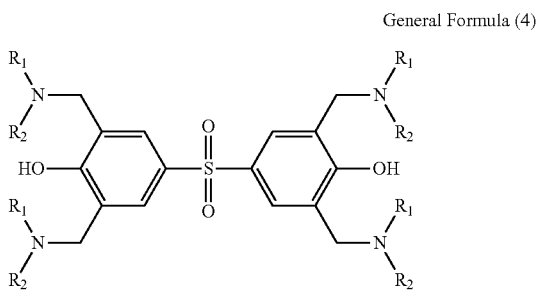

General Formula (4)

(wherein, $R_1$ and $R_2$ are the same as those of General Formula (3)).

Specific examples of such an aminomethyl-substituted bisphenol compound represented by General Formula (4) shown above include bis[3,5-bis(dimethylaminomethyl)-4-hydroxyphenyl]sulfone, bis[3,5-bis(diethylaminomethyl)-4-hydroxyphenyl]sulfone, bis[3,5-bis(diisopropylaminomethyl)-4-hydroxyphenyl]sulfone, and bis[3,5-bis(morpholinomethyl)-4-hydroxyphenyl]sulfone.

In the aminomethylation reaction (step 1), the molar ratio of formaldehyde and the secondary amine to the raw material bisphenol compound is preferably a stoichiometric amount or more, and specifically, the molar ratio of the secondary amine to the raw material bisphenol compound is preferably in the range of 4 to 40 molar times and more preferably in the range of 5 to 15 molar times, and similarly, the molar ratio of formaldehyde to the raw material bisphenol compound is preferably in the range of 4 to 40 molar times and more preferably in the range of 5 to 15 molar times.

In the reaction, a reaction solvent may or may not be used. When a reaction solvent is used, the reaction solvent is not particularly limited as long as the reaction solvent is a known solvent for the reaction, and specific examples thereof include water, ether solvents such as diethyl ether, dibutyl ether, and tetrahydrofuran, alcohol solvents such as methanol, ethanol, propanol, and butanol, aromatic hydrocarbon solvents such as toluene and xylene, ketone solvents such as acetone and methyl isobutyl ketone, ester solvents such as ethyl acetate and γ-butyrolactone, nitrile solvents such as acetonitrile, and aprotic polar solvents such as N-methyl pyrrolidone, N-methyl-2-pyrrolidone, N,N-dimethylformamide, and N,N-dimethylacetamide. Such solvents may be used alone or in combination of two or more.

The amount of the solvent used is not particularly limited, but is preferably in the range of 0.5 to 20 parts by weight and more preferably in the range of 1 to 5 parts by weight with respect to 1 part by weight of the bisphenol compound represented by Chemical Formula (2).

The reaction temperature of the aminomethylation reaction is preferably in the range of 0 to 120° C. (up to the reflux temperature of the solvent) and more preferably 25 to 100° C. (up to the reflux temperature of the solvent), and the reaction temperature may be appropriately selected in the temperature range described above.

The reaction time is normally about 0.5 to 24 hours and preferably about 1 to 10 hours.

In addition, in the aminomethylation reaction, the addition order of the raw materials is not particularly limited. For example, the raw material bisphenol compound, the secondary amine, the aqueous solution of formaldehyde, and a solvent if necessary may be simultaneously added, or the aqueous solution of formaldehyde may be added dropwise after adding the raw material bisphenol compound and the secondary amine.

After completion of the aminomethylation reaction of the above bisphenol compound with formaldehyde and the secondary amine (step 1), the aminomethyl-substituted bisphenol compound, which is a target reaction product, is separated and collected from the reaction mixture obtained by a known method, and can be used as a raw material for the next step.

For example, after completion of the reaction, a solvent which separates from water such as toluene, xylene, methyl isobutyl ketone, or ether is added to the reaction-completed mixture as necessary, and then the aqueous layer is separated. Water may be added to the obtained oil layer to wash the oil layer with water, the solvent may be removed from the oil layer by distillation or the like as needed, and thus a crude product containing the target product obtained thereby may be used as the raw material for the next step as it is. In addition, a method of pouring the reaction-completed liquid into water for precipitation may be used, or the oil layer obtained by washing with water may be crystallized and filtered to isolate the aminomethyl-substituted bisphenol compound as a reaction product.
<Step 2>
Next, the aminomethyl-substituted bisphenol compound obtained in the step 1 described above is acyloxylated to obtain an acyloxy-substituted bisphenol compound. In the acyloxylation (step 2), the reaction can be easily carried out according to a known acyloxylation method in which an aminomethyl compound is reacted with a carboxylic acid anhydride. In the acyloxylation (step 2) according to the present invention, examples of the carboxylic acid anhydride include acetic anhydride, propionic anhydride, and butyric anhydride with preference given to acetic anhydride. Accordingly, the acyloxy-substituted bisphenol compound obtained in the step 2 is preferably a compound represented by Formula (5) below.

[Chem. 7]

Formula (5)

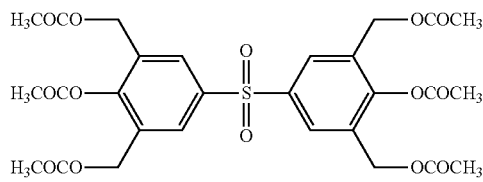

In the acyloxylation (step 2), the molar ratio of acetic anhydride to the aminomethyl-substituted bisphenol compound as an intermediate raw material is preferably a stoichiometric amount or more, and specifically, the molar ratio of acetic anhydride to the aminomethyl-substituted bisphenol compound is preferably in the range of 6 to 40 molar times and more preferably in the range of 6 to 20 molar times.

Although it is not particularly necessary to use other solvents because acetic anhydride also serves as a solvent, non-aqueous solvents such as toluene and xylene may be used as necessary for the reaction operation.

Normally, the reaction temperature is preferably in the range of 0 to 120° C. and more preferably in the range of 25 to 100° C.

The reaction time is normally about 0.5 to 40 hours and preferably about 5 to 20 hours.

After completion of the reaction, an acyloxy-substituted bisphenol compound, which is a target reaction product, can be separated and collected from the obtained reaction-completed mixture by a known method, and can be used as a raw material for the next step. For example, after completion of the reaction, unreacted acetic anhydride, the solvent added as necessary, and the like may be distilled from the reaction-completed mixture to obtain a crude product containing the target product, and the obtained crude product may be used as a raw material for the next step as it is. Alternatively, the obtained crude product may be dissolved in an appropriate solvent, crystallized, and filtered to isolate the acyloxy-substituted bisphenol compound, which is a reaction product.

<Step 3>

Next, the acyloxy-substituted bisphenol compound obtained in the step 2 is reacted with an alkyl alcohol in the presence of an acidic or alkaline catalyst to alkoxymethylate an acyloxy group (step 3), and thus the alkoxymethyl-substituted bisphenol compound represented by General Formula (1) of the present invention is obtained.

The alkyl alcohol used in the alkoxymethylation (step 3) is represented by General Formula (6) below General Formula (6)

R—OH  [Chem. 8]

(wherein R is the same as that of General Formula (1)).

Specific examples of the alkyl alcohol represented by General Formula (6) include methanol, ethanol, and isopropanol.

The amount of the alkyl alcohol used is preferably the stoichiometric amount or more in molar ratio with respect to the acyloxy-substituted bisphenol compound serving as the intermediate raw material, and is usually used in excess with respect to the acyloxy-substituted bisphenol compound while also serving as a reaction solvent. The amount is not particularly limited as long as the amount is the stoichiometric amount or more, but is specifically, for example, in the range of 6 to 2000 molar times.

The reaction is usually carried out in the presence of a catalyst. Specific examples of the catalyst used include, for example, acid catalysts such as sulfuric acid and p-toluenesulfonic acid, alkali catalysts such as potassium carbonate, sodium carbonate, potassium hydroxide, sodium hydroxide, and sodium methylate, and carboxylic acid salts such as sodium acetate and potassium acetate. Preferably, the catalyst is an acid catalyst. The appropriate amount of catalyst used varies depending on the type of catalyst. In the case of sulfuric acid, the amount is preferably in the range of 0.01 to 1 mol and more preferably 0.05 to 0.5 mol with respect to 1 mol of the alkyl alcohol.

Although it is not particularly necessary to use other solvents in a usual situation because the alkyl alcohol also serves as a solvent, non-aqueous solvents such as toluene and xylene may be used as necessary for the reaction operation.

The reaction temperature is preferably in the range of 0 to 100° C. (up to the reflux temperature of the solvent) and more preferably in the range of 25 to 100° C. (up to the reflux temperature of the solvent).

The reaction time is usually about 1 to 240 hours and preferably about 5 to 100 hours.

In addition, in the alkoxymethylation reaction, the addition order of the raw materials is not particularly limited. For example, the acyloxy-substituted bisphenol compound, the alkyl alcohol, and the catalyst may be added simultaneously, or the acyloxy-substituted bisphenol compound may be added after mixing the alkyl alcohol and the catalyst.

After completion of the above alkoxymethylation reaction (step 3), the alkoxymethyl-substituted bisphenol compound of the present invention, which is a target reaction product, is separated and purified from the obtained reaction-completed mixture according to a conventional method, and thus can be isolated as a crude product or a high-purity product.

For example, in the case of using an acid catalyst, after completion of the reaction, an alkali is added to the reaction-completed mixture to neutralize, and if necessary, a solvent which separates from water is added to wash with water after distilling off excess alkyl alcohol and so forth, the solvent is removed by distillation or the like if necessary, and thus the target product can be obtained as a crude product. In addition, by further purifying the crude product by a purification method including crystallization and filtration or by column chromatography, a high-purity product of the alkoxymethyl-substituted bisphenol compound of the present invention, which is the target product, can be obtained.

EXAMPLES

Hereinafter, the present invention will be described in further detail with reference to examples.

Example 1

Synthesis of Bis[3,5-bis(methoxymethyl)-4-hydroxyphenyl]sulfone

Step 1

Synthesis of Bis[3,5-bis(diethylaminomethyl)-4-hydroxyphenyl]sulfone

In a 1-liter four-necked flask equipped with a thermometer, a stirrer, a dropping funnel, and a condenser, 74.8 g (0.3 mol) of bis(4-hydroxyphenyl)sulfone, 192.5 g (2.6 mol) of diethylamine, and 225.7 g (2.6 mol) of 35% aqueous solution of formalin were charged, and reaction was carried out while stirring the system for 2 hours while maintaining the internal temperature at 80 to 85° C.

Subsequently, toluene and water are added to the obtained reaction liquid, and after stirring, an aqueous layer was separated, and then toluene and the like were distilled from an organic layer by distillation under reduced pressure to obtain bis[3,5-bis(diethylaminomethyl)-4-hydroxyphenyl]sulfone having a purity of 95.4% (high-performance liquid chromatography analysis, area %) as 195.9 g of a crude product.

Step 2

Synthesis of Bis[3,5-bis(acetoxymethyl)-4-acetoxyphenyl]sulfone

To 195.9 g of the crude product obtained in step 1, 267.0 g (2.6 mol) of acetic anhydride was added, and reaction was carried out while stirring the system for 14 hours while maintaining the internal temperature at 80 to 90° C.

Subsequently, unreacted acetic anhydride and the like were distilled from the obtained reaction liquid by distillation under reduced pressure, then methanol was added, crystal precipitated by a crystallization operation was filtrated, and thus 171.3 g of bis[3,5-bis(acetoxymethyl)-4-acetoxyphenyl]sulfone having a purity of 91.1% (high-performance liquid chromatography analysis, area %) was obtained.

Step 3

Synthesis of Bis[3,5-bis(methoxymethyl)-4-hydroxyphenyl]sulfone

In a 100-milliliter four-necked flask equipped with a thermometer, a stirrer, a dropping funnel, and a condenser, 500 mg (0.8 mmol) of bis[3,5-bis(acetoxymethyl)-4-acetoxyphenyl]sulfone obtained in step 2, 50 g of methanol, and 10 g of 98% sulfuric acid were charged, and reaction was carried out while stirring the system for 72 hours while maintaining the internal temperature at 60 to 62° C.

Next, sodium hydroxide and phosphoric acid were added to the obtained reaction liquid, and then the solvent was distilled off. After adding butyl acetate and water to the obtained crude product and performing an operation of separating an aqueous layer after stirring, butyl acetate and the like were distilled from an organic layer by distillation under reduced pressure. The obtained crude product was subjected to separation operation by silica gel column chromatography, and thus 204 mg of bis[3,5-bis(methoxymethyl)-4-hydroxyphenyl]sulfone having a purity of 93.9% (high performance liquid chromatography analysis, area %) was obtained.

Yield: 59.5 mol % (vs. acetoxy-substituted bisphenol compound)

$^1$H-NMR (400 MHz, solvent: CDCl$_3$, standard TMS): 3.45 ppm (s, 12H), 4.60 ppm (s, 8H), 7.70 ppm (s, 4H), 8.52 ppm (s, 2H).

Reference Example 1

Synthesis of Compound A

Reaction was carried out in the same manner as in Example 1 except that bis(4-hydroxyphenyl) sulfide was used instead of bis(4-hydroxyphenyl)sulfone of Example 1, and thus Compound A was isolated and purified from the obtained reaction composition.

Reference Example 2

Synthesis of Compound B

Reaction was carried out in the same manner as in Example 1 except that bis(4-hydroxyphenyl) ether was used instead of bis(4-hydroxyphenyl)sulfone of Example 1, and thus Compound B was isolated and purified from the obtained reaction composition.

Example 2

Comparison of Physical Properties with Similar Compounds by Thermal Analysis

Thermogravimetric analysis of the bis[3,5-bis(methoxymethyl)-4-hydroxyphenyl]sulfone obtained in Example 1 and Compound A and Compound B below was carried out according to the following conditions, and the temperature and melting point at each weight loss ratio are shown in Table 1.

(Thermogravimetric Analysis Conditions)

Apparatus: differential thermal/thermogravimetric analyzer DTG-60A manufactured by Shimadzu Corporation Measurement condition: 30° C.→10° C./min→500° C.

Amount of sample: 10 mg

Atmospheric gas: nitrogen

Gas flow rate: 50 ml/min

[Chem. 9]

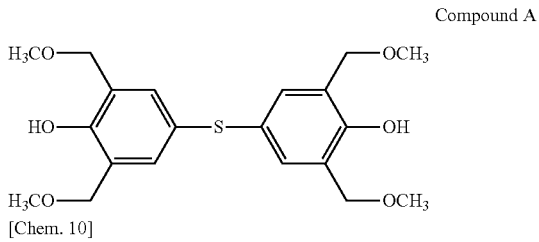

Compound A

[Chem. 10]

-continued

Compound B

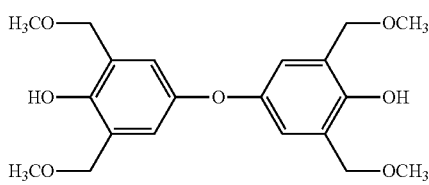

TABLE 1

|  | Melting point (° C.) | Thermal amount reduction (° C.) | |
|---|---|---|---|
|  |  | −10% | −20% |
| Compound of Example 1 | 127.3 | 234.2 | 289.0 |
| Compound A | 51.1 | 194.2 | 219.7 |
| Compound B | 78.2 | 235.9 | 262.1 |

From the results of the thermogravimetric analysis in Table 1, it has been confirmed that the bis[3,5-bis(methoxymethyl)-4-hydroxyphenyl]sulfone compound of the present invention has a high thermal weight reduction temperature and high thermal stability and high heat resistance as compared to Compound A and Compound B that are known. In addition, the compound of the present invention has a higher melting point than Compound A that is conventionally known, and unlike Compound A having a low melting point, can be crystallized by crystallization or the like. Further, since the compound of the present invention can be further purified by the crystallization, the compound of the present invention is also excellent in storage stability and so forth.

The invention claimed is:

1. An alkoxymethyl-substituted bisphenol compound represented by General Formula (1):

General Formula (1)

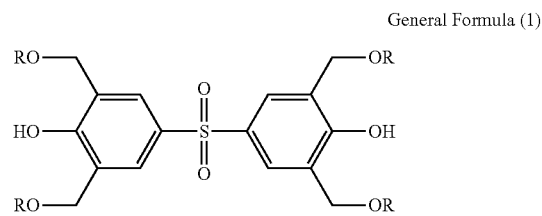

wherein each R independently represents an alkyl group having 1 to 4 carbon atoms.

* * * * *